(12) United States Patent
Chang

(10) Patent No.: US 11,661,450 B2
(45) Date of Patent: May 30, 2023

(54) COMBINATION THERAPY USING AN IL-20 ANTAGONIST AND AN IMMUNE CHECKPOINT INHIBITOR

(71) Applicant: LBL Biotechnology Inc., Tainan (TW)

(72) Inventor: Ming-Shi Chang, Tainan (TW)

(73) Assignee: LBL Biotechnology Inc., Tainan (TW)

( * ) Notice: Subject to any disclaimer, the term of this patent is extended or adjusted under 35 U.S.C. 154(b) by 321 days.

(21) Appl. No.: 16/855,637

(22) Filed: Apr. 22, 2020

(65) Prior Publication Data

US 2021/0332121 A1    Oct. 28, 2021

(51) Int. Cl.
*C07K 16/24* (2006.01)
*C07K 16/28* (2006.01)
*A61P 35/00* (2006.01)

(52) U.S. Cl.
CPC ............ *C07K 16/244* (2013.01); *A61P 35/00* (2018.01); *C07K 16/2818* (2013.01); *C07K 16/2827* (2013.01); *C07K 2317/24* (2013.01); *C07K 2317/565* (2013.01); *C07K 2317/622* (2013.01)

(58) Field of Classification Search
None
See application file for complete search history.

(56) References Cited

U.S. PATENT DOCUMENTS

| | | |
|---|---|---|
| 8,603,470 B1 | 12/2013 | Chang |
| 2013/0315893 A1 | 11/2013 | Chang et al. |
| 2016/0289341 A1* | 10/2016 | Wu .......................... A61P 25/16 |
| 2017/0349656 A1* | 12/2017 | Chang ..................... A61P 35/00 |

\* cited by examiner

*Primary Examiner* — Laura B Goddard
*Assistant Examiner* — Sarah A Alsomairy
(74) *Attorney, Agent, or Firm* — McDermott Will & Emery LLP

(57) ABSTRACT

Methods and compositions relating to combination therapy using an IL-20 antagonist and an immune checkpoint inhibitor are provided.

11 Claims, 2 Drawing Sheets

Specification includes a Sequence Listing.

Combined blockade of IL-20 and PD1 inhibited murine pancreatic tumor mass of PDAC orthotopic model

SEQUENCE LISTING

<160> NUMBER OF SEQ ID NOS: 13

<210> SEQ ID NO 1
<211> LENGTH: 363
<212> TYPE: DNA
<213> ORGANISM: Artificial sequence
<220> FEATURE:
<223> OTHER INFORMATION: Synthetic polynucleotide

<400> SEQUENCE: 1
gaattgaagc ttgaggagtc tggaggaggc ttggtgcagc ctggaggatc catgaaactc    60
tcttgtgctg cctctggatt cacttttagt gacgcctgga tggactgggt ccgccagtct   120
ccagagaagg ggcttgagtg gattgctgaa attagaagca aagctaataa ttatgcaaca   180
tactttgctg agtctgtgaa agggaggttc accatctcaa gagatgattc caaaagtggt   240
gtctacctgc aaatgaacaa cttaagagct gaggacactg gcatttattt ctgtaccaag   300
ttatcactac gttactggtt cttcgatgtc tggggcgcag ggaccacggt caccgtctcc   360
tca                                                                 363

<210> SEQ ID NO 2
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 2

Glu Leu Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Ile
        35                  40                  45

Ala Glu Ile Arg Ser Lys Ala Asn Asn Tyr Ala Thr Tyr Phe Ala Glu
    50                  55                  60

Ser Val Lys Gly Arg Phe Thr Ile Ser Arg Asp Asp Ser Lys Ser Gly
65                  70                  75                  80

Val Tyr Leu Gln Met Asn Asn Leu Arg Ala Glu Asp Thr Gly Ile Tyr
                85                  90                  95

Phe Cys Thr Lys Leu Ser Leu Arg Tyr Trp Phe Phe Asp Val Trp Gly
            100                 105                 110

Ala Gly Thr Thr Val Thr Val Ser Ser
        115                 120

<210> SEQ ID NO 3
<211> LENGTH: 339
<212> TYPE: DNA
<213> ORGANISM: Artificial sequence
<220> FEATURE:
<223> OTHER INFORMATION: Synthetic polynucleotide

<400> SEQUENCE: 3
gattttgtga tgacccagac tccactcact ttgtcggtta ccattggaca accagcctcc    60
atctcttgca agtcaagtca gagcctcttg gatagtgatg aaagacata tttgaattgg    120 ttgttacaga ggccaggcca gtctccaaag cacctcatct atctggtgtc taaactggac   180
tctggagtcc ctgacaggtt cactggcagt ggatcaggga ccgatttcac actgagaatc   240
agcagagtgg aggctgagga tttgggagtt tattattgct ggcaaagtac acattttccg   300
tggacgttcg gtggaggcac caagctggaa atcaaacgg                          339

<210> SEQ ID NO 4
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 4

Asp Phe Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys His Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Arg Ile
65                  70                  75                  80

Ser Arg Val Glu Ala Glu Asp Leu Gly Val Tyr Tyr Cys Trp Gln Ser
                85                  90                  95

Thr His Phe Pro Trp Thr Phe Gly Gly Gly Thr Lys Leu Glu Ile Lys
            100                 105                 110

Arg

<210> SEQ ID NO 5
<211> LENGTH: 420
<212> TYPE: DNA
<213> ORGANISM: Artificial sequence
<220> FEATURE:
<223> OTHER INFORMATION: nucleotide sequence encoding the amino acid
      sequence of SEQ ID NO:6

<400> SEQUENCE: 5
atgtacttgg gactgaacta tgtttttcatc gtttttctcc tgaatggtgt ccagagtgaa    60
gtgcagcttg tggagtctgg aggaggcttg gtgcagcctg gaggatccct gaaactctct   120
tgtgctgcct ctggattcac ttttagtgac gcctggatgg actgggtccg ccaggcttcc   180
gggaaggggc ttgagtggat tgctgaaatt agaagcaaag ctaataatta tgcaacatac   240
tttgctgagt ctgtgaaagg gaggttcacc atctcaagag atgattccaa aaacaccgcc   300
tacctgcaaa tgaacagctt aaaaaccgag gacactgccg tttattactg taccaagtta   360
tcactgcgtt actggttctt cgatgtctgg ggccagggga ccctggtcac cgtctcctca   420

<210> SEQ ID NO 6
<211> LENGTH: 140
<212> TYPE: PRT
<213> ORGANISM: Artificial sequence
<220> FEATURE:
<223> OTHER INFORMATION: the amino acid sequence of the precursor VH
      chain variable region of exemplary humanized anti-IL-20 antibodies
      HL1 and HL2

<400> SEQUENCE: 6

Met Tyr Leu Gly Leu Asn Tyr Val Phe Ile Val Phe Leu Leu Asn Gly
1               5                   10                  15

Val Gln Ser Glu Val Gln Leu Val Glu Ser Gly Gly Gly Leu Val Gln
            20                  25                  30

```
Pro Gly Gly Ser Leu Lys Leu Ser Cys Ala Ala Ser Gly Phe Thr Phe
            35                  40                  45

Ser Asp Ala Trp Met Asp Trp Val Arg Gln Ala Ser Gly Lys Gly Leu
 50                  55                  60

Glu Trp Ile Ala Glu Ile Arg Ser Lys Ala Asn Asn Tyr Ala Thr Tyr
 65                  70                  75                  80

Phe Ala Glu Ser Val Lys Gly Arg Phe Thr Ile Ser Arg Asp Asp Ser
                 85                  90                  95

Lys Asn Thr Ala Tyr Leu Gln Met Asn Ser Leu Lys Thr Glu Asp Thr
            100                 105                 110

Ala Val Tyr Tyr Cys Thr Lys Leu Ser Leu Arg Tyr Trp Phe Phe Asp
            115                 120                 125

Val Trp Gly Gln Gly Thr Leu Val Thr Val Ser Ser
130                 135                 140

<210> SEQ ID NO 7
<211> LENGTH: 363
<212> TYPE: DNA
<213> ORGANISM: Artificial sequence
<220> FEATURE:
<223> OTHER INFORMATION: the nucleotide sequence encoding the amino acid
      sequence of SEQ ID NO:8

<400> SEQUENCE: 7
gaagtgcagc ttgtggagtc tggaggaggc ttggtgcagc ctggaggatc cctgaaactc      60
tcttgtgctg cctctggatt cactttagt gacgcctgga tggactgggt ccgccaggct     120
tccgggaagg ggcttgagtg gattgctgaa attagaagca agctaataa ttatgcaaca     180 tactttgctg agtctgtgaa agggaggttc accatctcaa gagatgattc caaaaacacc     240
gcctacctgc aaatgaacag cttaaaaacc gaggacactg ccgttttatta ctgtaccaag     300 ttatcactgc gttactggtt cttcgatgtc tggggccagg ggaccctggt caccgtctcc     360
tca                                                                   363

<210> SEQ ID NO 8
<211> LENGTH: 121
<212> TYPE: PRT
<213> ORGANISM: Artificial sequence
<220> FEATURE:
<223> OTHER INFORMATION: the amino acid sequence of the mature VH chain
      variable region (which lacks the signal peptide) of the exemplary
      humanized anti-IL-20 antibodies HL1 and HL2

<400> SEQUENCE: 8

Glu Val Gln Leu Val Glu Ser Gly Gly Gly Leu Val Gln Pro Gly Gly
 1               5                  10                  15

Ser Leu Lys Leu Ser Cys Ala Ala Ser Gly Phe Thr Phe Ser Asp Ala
            20                  25                  30

Trp Met Asp Trp Val Arg Gln Ala Ser Gly Lys Gly Leu Glu Trp Ile
            35                  40                  45

Ala Glu Ile Arg Ser Lys Ala Asn Asn Tyr Ala Thr Tyr Phe Ala Glu
 50                  55                  60

Ser Val Lys Gly Arg Phe Thr Ile Ser Arg Asp Asp Ser Lys Asn Thr
 65                  70                  75                  80

Ala Tyr Leu Gln Met Asn Ser Leu Lys Thr Glu Asp Thr Ala Val Tyr
                 85                  90                  95

Tyr Cys Thr Lys Leu Ser Leu Arg Tyr Trp Phe Phe Asp Val Trp Gly
            100                 105                 110
```

```
Gln Gly Thr Leu Val Thr Val Ser Ser
        115                 120
```

<210> SEQ ID NO 9
<211> LENGTH: 396
<212> TYPE: DNA
<213> ORGANISM: Artificial sequence
<220> FEATURE:
<223> OTHER INFORMATION: the nucleotide sequence encoding the amino acid
      sequence of SEQ ID NO:10

<400> SEQUENCE: 9

```
atgatgagtc ctgcccagtt cctgtttctg ttggtgctct ggattcggga aaccaacggt    60
gatatcgtga tgacccagac tccactctct ttgtccgtta ccctggaca  accagcctcc   120 atctcttgca gtcaagtca  gagcctcttg gatagtgatg gaaagacata tttgaattgg   180
ttgttacaga agccaggcca gtctccacag cacctcatct atctggtgtc taaactggac   240
tctggagtcc ctgacaggtt cagtggcagt ggatcaggga ccgatttcac actgaaaatc   300
agcagagtgg aggctgagga tgttggagtt tattattgct ggcaaagtac acattttccc   360
tggaccttcg gtggaggcac caaggtggaa atcaaa                             396
```

<210> SEQ ID NO 10
<211> LENGTH: 132
<212> TYPE: PRT
<213> ORGANISM: Artificial sequence
<220> FEATURE:
<223> OTHER INFORMATION: the amino acid sequence of the precursor VL
      chain variable region of exemplary humanized anti-IL-20 antibody
      HL2

<400> SEQUENCE: 10

```
Met Met Ser Pro Ala Gln Phe Leu Phe Leu Leu Val Leu Trp Ile Arg
1               5                   10                  15

Glu Thr Asn Gly Asp Ile Val Met Thr Gln Thr Pro Leu Ser Leu Ser
            20                  25                  30

Val Thr Pro Gly Gln Pro Ala Ser Ile Ser Cys Lys Ser Ser Gln Ser
        35                  40                  45

Leu Leu Asp Ser Asp Gly Lys Thr Tyr Leu Asn Trp Leu Leu Gln Lys
    50                  55                  60

Pro Gly Gln Ser Pro Gln His Leu Ile Tyr Leu Val Ser Lys Leu Asp
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Val Gly Val Tyr Tyr
            100                 105                 110

Cys Trp Gln Ser Thr His Phe Pro Trp Thr Phe Gly Gly Gly Thr Lys
        115                 120                 125

Val Glu Ile Lys
    130
```

<210> SEQ ID NO 11
<211> LENGTH: 336
<212> TYPE: DNA
<213> ORGANISM: Artificial sequence
<220> FEATURE:
<223> OTHER INFORMATION: the nucleotide sequence encoding the amino acid
      sequence of SEQ ID NO:12

<400> SEQUENCE: 11

```
gatatcgtga tgacccagac tccactctct ttgtccgtta ccctggaca  accagcctcc    60
```

```
atctcttgca agtcaagtca gagcctcttg gatagtgatg gaaagacata tttgaattgg    120
ttgttacaga agccaggcca gtctccacag cacctcatct atctggtgtc taaactggac    180
tctggagtcc ctgacaggtt cagtggcagt ggatcaggga ccgatttcac actgaaaatc    240
agcagagtgg aggctgagga tgttggagtt tattattgct ggcaaagtac acattttccc    300
tggaccttcg gtggaggcac caaggtggaa atcaaa                              336
```

<210> SEQ ID NO 12
<211> LENGTH: 112
<212> TYPE: PRT
<213> ORGANISM: Artificial sequence
<220> FEATURE:
<223> OTHER INFORMATION: the amino acid sequence of the mature VL chain
      variable region (which lacks the signal peptide) of exemplary
      humanized anti-IL-20 antibody HL2

<400> SEQUENCE: 12

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln His Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Ser
                85                  90                  95

Thr His Phe Pro Trp Thr Phe Gly Gly Gly Thr Lys Val Glu Ile Lys
            100                 105                 110
```

<210> SEQ ID NO 13
<211> LENGTH: 112
<212> TYPE: PRT
<213> ORGANISM: Artificial sequence
<220> FEATURE:
<223> OTHER INFORMATION: identical to the VL of HL2 except that the I
      residue at position 2 of mature VL of HL2 is replaced with F

<400> SEQUENCE: 13

```
Asp Phe Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Lys Pro Gly Gln Ser
        35                  40                  45

Pro Gln His Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Ser
                85                  90                  95

Thr His Phe Pro Trp Thr Phe Gly Gly Gly Thr Lys Val Glu Ile Lys
            100                 105                 110
```

COMBINATION THERAPY USING AN IL-20 ANTAGONIST AND AN IMMUNE CHECKPOINT INHIBITOR

SEQUENCE LISTING

This instant application contains a Sequence Listing which has been submitted electronically in ASCII format and is hereby incorporated by reference in its entirety. Said ASCII copy, created on Aug. 24, 2020, is named G4590-07700US SeqListing.txt and is 13 kilobytes in size.

FIELD OF THE INVENTION

The present disclosure relates to methods and compositions for a combination therapy comprising an IL-20 antagonist and an immune checkpoint inhibitor; more specifically the disclosure is directed to methods for treating and/or preventing a cancer or a fibrosis.

BACKGROUND OF THE INVENTION

PD-1 (Programmed Cell Death Protein 1) binds to PD-L1 (Programmed Cell Death Ligand-1) and their binding interactions play a role in the regulation of the immune system functions, including immunity and self-tolerance. PD-L1 is expressed in tumors, and upregulation of PD-L1 can allow cancers to evade the host immune system. Thus, interfering with the inhibitory signal through the PD-L1:PD-1 pathway is a therapeutic option for enhancing anti-tumor immunity. Antibodies blocking the activation of the programmed cell death 1 (PD-1) receptor have been found to be effective in improving the immune cells targeting of cancer cells, however, long lasting responses are only observed in a small subset of immunotherapy-treated patients.

Interleukin IL-20 (IL-20) is a member of the IL-10 family, which includes IL-10, IL-19, IL-20, IL-22, IL-24, and IL-26. Blumberg, et al., 2001, Cell 104:9-19; Pestka et al., 2004, Annu Rev Immunol 22:929-979. IL-20 is expressed in monocytes, epithelial cells, and endothelial cells and acts on multiple cell types by activating a heterodimer receptor complex of either IL-20R1/IL-20R2 or IL-22R1/IL-20R2. Dumoutier, et al., 2001, J Immunol 167:3545-3549). IL-20 was found to be involved in various inflammatory diseases, such as psoriasis (Blumberg et al., 2001; Sa et al., 2007, J Immunol 178:2229-2240; and Wei et al., 2005, Clin Immunol 117:65-72), rheumatoid arthritis (Hsu, et al., 2006, Arthritis Rheum 54:2722-2733), atherosclerosis (Caligiuri, et al. 2006, Arterioscler Thromb Vasc Biol 26:1929-1930; and Chen et al., 2006, Arterioscler Thromb Vasc Biol 26:2090-2095), ischemic stroke (Chen et al., 2009, J Immunol 182:5003-5012), and renal failure (Li et al., 2008, Genes Immun 9:395-404). See also Wei et al., 2006, J Biomed Sci 13:601-612.

There remains a need to increase the efficacy of oncology treatments.

SUMMARY OF THE INVENTION

The present disclosure is based on the unexpected results that anti-IL-20 antibodies in combination with immune checkpoint inhibitors successfully inhibited tumor growth and prolonged survival rates. Also, the combination of anti-human IL-20 antibodies in combination with immune checkpoint inhibitors have unexpected efficacy in treatment or prevention or reversal of a tissue fibrosis.

Accordingly, one aspect of the present disclosure relates to a method for treating a cancer or a fibrosis or delaying the onset of a cancer or a fibrosis in a subject, comprising administering to a subject in need of the treatment an effective amount of a combination comprising an IL-20 antagonist and an immune checkpoint inhibitor.

Another aspect of the present disclosure relates to a method for treating or preventing a tissue fibrosis, comprising administering to a subject in need thereof an effective amount of a combination comprising an IL-20 antagonist and an immune checkpoint inhibitor.

In some embodiments, the IL-20 antagonist can be an antibody that binds to IL-20 or an IL-20 receptor, thereby inhibiting a signaling pathway mediated by IL-20. For example, such an antibody may bind to an IL-20 protein (e.g., human IL-20) or may bind to an IL-20 receptor (e.g., a human IL-20 receptor such as R1 subunit of an IL-20). Any of the exemplary antibodies used in the method described herein can be a full-length antibody or an antigen-binding fragment thereof. Alternatively, the antibody can be a human antibody, a humanized antibody, a chimeric antibody, or a single-chain antibody.

In one aspect, an exemplary antibody that binds human IL-20 used herein can be a monoclonal antibody mAb7E, an antigen-binding fragment thereof, or a functional variant thereof. In one example, a functional variant of mAb7E comprises the same complementary determining regions (CDRs) as mAb7E. In another example, the functional variant is a humanized antibody of mAb7E. Such a humanized antibody can comprises a heavy chain variable region ($V_H$), which comprises the amino acid sequence of SEQ ID NO:8, and a light chain variable region ($V_L$), which comprises the amino acid sequence of SEQ ID NO:12 or SEQ ID NO:13.

In one aspect, the exemplary immune checkpoint inhibitor contemplated in accordance with the method described herein, can include, for example, an anti-CTLA-4 antibody, anti-PD-1 antibody or an anti-PD-L1 antibody. Certain embodiments of the immune checkpoint inhibitor include pembrolizumab, pidilizumab, nivolumab, durvalumab, avelumab, atezolizumab, toripalimab, sintilimab, camrelizumab, and MIHI.

The subject to be treated in the method described herein can be a patient (e.g., a human patient) who has or is suspected of having a cancer. In some examples, the subject is a human patient who has or is suspected of having a cancer.

Exemplary cancers treated by the methods embodiments described herein include pancreatic cancer, glioblastoma, liver cancer, colorectal carcinoma, glioblastoma, gastric cancer, colorectal cancer, esophageal cancer, lung cancer, renal cell carcinoma, benign prostate hyperplasia, prostate cancer, ovarian cancer, melanoma, breast cancer, chronic lymphocytic leukemia (CLL), Merkel cell carcinoma, Non-Hodgkin lymphoma, acute myeloid leukemia (AML), gallbladder cancer, cholangiocarcinoma, urinary bladder cancer, and uterine cancer. In one embodiment, the pancreatic cancer is pancreatic adenocarcinoma or non-adenocarcinoma.

Exemplars of fibrosis to be treated by the method described herein include pulmonary fibrosis, idiopathic pulmonary fibrosis, Dupuytren disease, nonalcoholic steatohepatitis, portal hypertension, systemic sclerosis, renal fibrosis, cardiac fibrosis, and cutaneous fibrosis.

Also within the scope of this disclosure are (a) combinations for use in treating a cancer or delaying the onset of a cancer or a tissue fibrosis in a subject, the exemplary combination can comprise one or more of the IL-20 antagonists described herein and one or more immune checkpoint inhibitors; and (b) the uses of combinations described herein in manufacturing a medicament for treating or delaying the onset of a cancer.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

A more complete understanding of the invention may be obtained by reference to the accompanying drawings, when considered in conjunction with the subsequent detailed description. The embodiments illustrated in the drawings are intended only to exemplify the invention and should not be construed as limiting the invention to the illustrated embodiments.

The subject patent application file contains at least one drawing executed in color. Copies of this patent or patent application publication with color drawing(s) will be provided by the Office upon request and payment of the necessary fee.

DETAILED DESCRIPTION OF THE INVENTION

Figure 1:
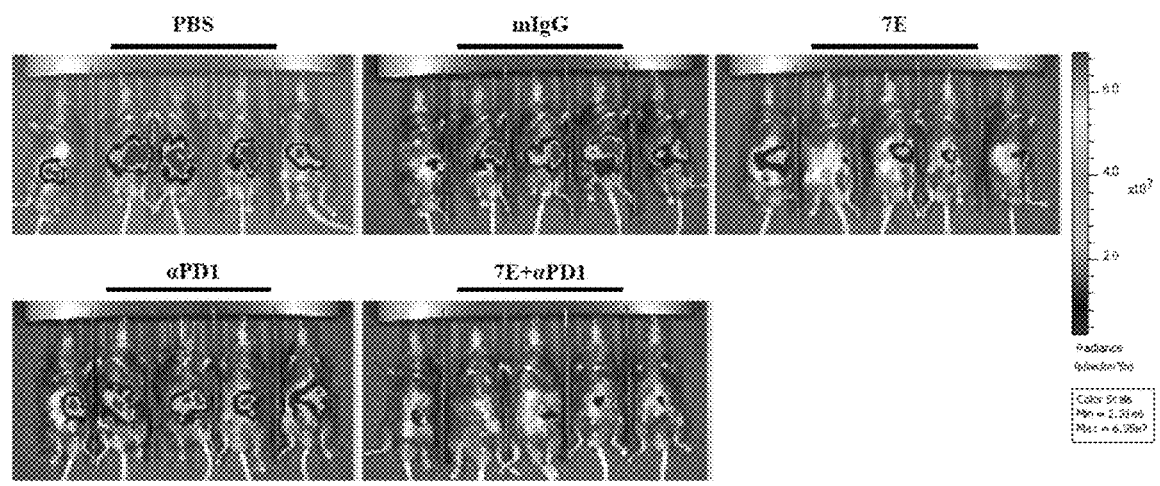
FIG. 1 shows how 7E and PD1 antibody combination therapy alleviated tumor progression in an orthotopic model of PDAC.

The present disclosure reports the unexpected results that an antibody capable of interfering with the IL-20 signaling pathway (e.g., anti-IL-20 antibody such as mAb7E) in combination with an immune checkpoint inhibitor successfully inhibited tumor growth and prolonged survival rates. Accordingly, the present disclosure relates to methods of treating a cancer (e.g., alleviating a cancer or delaying the onset of a cancer) in a subject using an effective amount of an IL-20 antagonist in combination with an effective amount of an immune checkpoint inhibitor.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

IL-20 Antagonists

Exemplary IL-20 can include a pro-inflammatory cytokine that belongs to the IL-10 cytokine family. The IL-20 described herein refers to interleukin-20 and variants thereof that retain at least part of the activity of IL-20. As used herein, IL-20 includes all mammalian species of native sequence IL-20, including human, canine, feline, equine, or bovine. In one example, the IL-20 is a human IL-20 (GenBank accession no. NP 061194.2).

IL-20 activates the IL-20 signaling pathway via binding to IL-20 receptor, which is a dimeric complex contains subunits IL-20R1 and IL-20R2 (also known as RA and RB). Such an IL-20 receptor is shared by three functionally different cytokines, i.e., IL-19, IL-20, and IL-24, suggesting that this receptor mediates different signaling pathways dependent upon its binding to a specific cytokine. IL-20 is also capable of binding to a dimeric complex containing IL-20R2 and IL-22R1. The IL-20 receptor disclosed herein refers to one or more polypeptides that are capable of binding to and being activated by IL-20. IL-20 receptors disclosed herein include IL-20R1, IL-20R2 and IL-22R1 of any mammalian species, including, but are not limited to, human, canine, feline, equine, primate, or bovine. Examples of human IL-20 receptors include hIL-20R1 (GenBank Accession No. NM_014432.2), hIL-20R2 (GenBank Accession No. NM_144717.2) and hIL-22R1 (NM_181309.1). Sequences of human IL-20 receptors have been described; for example, in U.S. Pat. Nos. 6,610,286; 7,122,632; 7,393, 684; and 7,537,761; and U.S. Pat. App. Pub. Nos. 2006/0263850 A1; 2006/0263851 A1; 2008/0247945 A1, and 2009/0074661 A1.

The IL-20 antagonist to be used in the methods described herein is a molecule that blocks, suppresses, or reduces (including significantly) the biological activity of IL-20, including downstream pathways mediated by IL-20 signaling, such as receptor binding and/or elicitation of a cellular response to IL-20. See US2011/0064731, which is incorporated by reference herein in its entirety. The term "antagonist" implies no specific mechanism of biological action whatsoever, and is deemed to expressly include and encompass all possible pharmacological, physiological, and biochemical interactions with IL-20 whether direct or indirect. For purpose of the present disclosure, it will be explicitly understood that the term "antagonist" encompass all the previously identified terms, titles, and functional states and characteristics whereby the IL-20 itself (e.g., human IL-20), an IL-20 biological activity (including but not limited to its ability to mediate any aspect of pancreatic cancer), or the consequences of the biological activity, are substantially nullified, decreased, or neutralized in any meaningful degree, e.g., by at least 20%, 50%, 70%, 85%, 90%, 100%, 150%, 200%, 300%, or 500%, or by 10-fold, 20-fold, 50-fold, 100-fold, 1000-fold, or 10. sup.4-fold.

Exemplary IL-20 antagonists include, but are not limited to, an anti-IL-20 antibody, an anti-sense nucleic acid molecule directed to an IL-20 (including an anti-sense nucleic acid directed to a nucleic acid encoding IL-20), a small interfering RNA (siRNA) directed toward an IL-20 nucleic acid, a microRNA directed toward an IL-20 nucleic acid, an IL-20 inhibitory compound, an anti-IL-20R antibody (e.g., an antibody specifically binds IL-20R1, IL-20R2, or the dimeric complex formed thereby), an antisense nucleic acid molecule directed to a subunit of an IL-20 receptor, an siRNA or a microRNA directed to a nucleic acid encoding a subunit of an IL-20 receptor, or an IL-20R inhibitory compound. In some embodiments, an IL-20 antagonist binds IL-20 or IL-20 receptor and prevents the formation of IL-20-IL-20R complex, thereby inhibiting the IL-20 signaling pathway. In other embodiments, an IL-20 antagonist inhibits or reduces IL-20 synthesis and/or production (release). Such antagonists include antisense molecules, siRNAs and microRNAs.

Antibodies Capable of Interfering with the IL-20 Signaling Pathway

An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab').sub.2, Fv), single chain (scFv), mutants thereof, fusion proteins comprising an antibody portion, humanized antibodies, chimeric antibodies, diabodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The antibodies used in the methods described herein can be murine, rat, human, or any other origin (including chimeric or humanized antibodies). In some examples, the antibody comprises a modified constant region, such as a constant region that is immunologically inert, e.g., does not trigger complement mediated lysis, or does not stimulate antibody-dependent cell mediated cytotoxicity (ADCC). ADCC activity can be assessed using methods disclosed in U.S. Pat. No. 5,500,362. In other embodiments, the constant region is modified as described in Eur. J. Immunol. (1999) 29:2613-2624; PCT Application No. PCT/GB99/01441; and/or UK Patent Application No. 9809951.8.

Any of the antibodies described herein can be either monoclonal or polyclonal. A "monoclonal antibody" refers to a homogenous antibody population and a "polyclonal antibody" refers to a heterogeneous antibody population. These two terms do not limit the source of an antibody or the manner in which it is made.

In one embodiment, the antibody used in the methods described herein is a humanized antibody. Humanized antibodies refer to forms of non-human (e.g., murine) antibodies that are specific chimeric immunoglobulins, immunoglobulin chains, or antigen-binding fragments thereof that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody. Humanized antibodies may also involve affinity maturation.

In another embodiment, the antibody described herein is a chimeric antibody, which can include a heavy constant region and a light constant region from a human antibody. Chimeric antibodies refer to antibodies having a variable region or part of variable region from a first species and a constant region from a second species. Typically, in these chimeric antibodies, the variable region of both light and heavy chains mimics the variable regions of antibodies derived from one species of mammals (e.g., a non-human mammal such as mouse, rabbit, and rat), while the constant portions are homologous to the sequences in antibodies derived from another mammal such as human. In some embodiments, amino acid modifications can be made in the variable region and/or the constant region.

In other embodiments, the antibody disclosed herein specifically binds a target antigen, such as human IL-20 or one of the two subunits of a human IL-20 receptor (e.g., IL-20R1). An antibody that "specifically binds" (used interchangeably herein) to a target or an epitope is a term well understood in the art, and methods to determine such specific binding are also well known in the art. A molecule is said to exhibit "specific binding" if it reacts or associates more frequently, more rapidly, with greater duration and/or with greater affinity with a particular target antigen than it does with alternative targets. An antibody "specifically binds" to a target antigen if it binds with greater affinity, avidity, more readily, and/or with greater duration than it binds to other substances. For example, an antibody that specifically (or preferentially) binds to an IL-20 epitope is an antibody that binds this IL-20 epitope with greater affinity, avidity, more readily, and/or with greater duration than it binds to other IL-20 epitopes or non-IL-20 epitopes. It is also understood by reading this definition that, for example, an antibody that specifically binds to a first target antigen may or may not specifically or preferentially bind to a second target antigen. As such, "specific binding" or "preferential binding" does not necessarily require (although it can include) exclusive binding. Generally, but not necessarily, reference to binding means preferential binding.

Antibodies capable of interfering with the IL-20 signaling pathway can be an antibody that binds an IL-20 (e.g., a human IL-20) and inhibits IL-20 biological activity and/or downstream pathways mediated by IL-20. Alternatively, such antibodies can be antibodies that bind an IL-20 receptor (IL-20R), e.g., bind to one or both of the subunits of the IL-20 receptor, and suppress the downstream signaling pathways mediated by the receptor triggered by IL-20.

(i) Anti-IL-20 Antibodies

An anti-IL-20 antibody is an antibody capable of binding to IL-20 and inhibits IL-20 biological activity and/or downstream pathway(s) mediated by IL-20 signaling. In some examples, an anti-IL-20 antibody used in the methods described herein suppresses the IL-20 signaling pathway by at least 20%, at least 40%, at least 50%, at least 75%, at least 90%, at least 100%, or by at least 2-fold, at least 5-fold, at least 10-fold, at least 20-fold, at least 50-fold, at least 100-fold, or at least 1000-fold. Examples of anti-IL-20 antibodies include, but are not limited to, those disclosed in U.S. Pat. Nos. 7,435,800; 7,115,714; 7,119,175; 7,151,166; and 7,393,684; and PCT publications WO 2007/081465; WO 99/27103; WO 2004/085475; and WO 2005052000.

The binding affinity of an anti-IL-20 antibody to IL-20 (such as human IL-20) can be less than any of about 100 nM, about 50 nM, about 10 nM, about 1 nM, about 500 pM, about 100 pM, or about 50 pM to any of about 2 pM. Binding affinity can be expressed K.sub.D or dissociation constant, and an increased binding affinity corresponds to a decreased $K_D$. One way of determining binding affinity of antibodies to IL-20 is by measuring binding affinity of monofunctional Fab fragments of the antibody. To obtain monofunctional Fab fragments, an antibody (for example, IgG) can be cleaved with papain or expressed recombinantly. The affinity of an anti-IL-20 Fab fragment of an antibody can be determined by surface plasmon resonance (BIAcore3000™ surface plasmon resonance (SPR) system, BIAcore, INC, Piscaway, N.J.). Kinetic association rates ($k_{on}$) and dissociation rates ($k_{off}$) (generally measured at 25.degree. C.) are obtained; and equilibrium dissociation constant ($K_D$) values are calculated as $k_{off}/k_{on}$.

In some embodiments, the antibody binds human IL-20, and does not significantly bind an IL-20 from another mammalian species. In some embodiments, the antibody binds human IL-20 as well as one or more IL-20 from another mammalian species. In still other embodiments, the antibody binds IL-20 and does not significantly cross-react with other cytokines (such as the related cytokines IL-10, IL-17A, IL-19, IL-22, IL-24 and IL-26). The epitope(s) bound by the antibody can be continuous or discontinuous.

In some embodiments, the anti-IL-20 antibody described herein is anti-IL-20 antibody 7E, which refers to monoclonal antibody mAb 7E and its functional variants. MAb 7E is produced by the hybridoma cell line deposited at the American Type Culture Collection, 10801 University Boulevard, Manassas, Va. 20110-2209, U.S.A. and assigned a deposit number PTA-8687. This hybridoma cell line will be released to the public irrevocably and without restriction/condition upon granting a US patent on this application, and will be maintained in the ATCC for a period of at least 30 years from the date of the deposit for the enforceable life of the patent or for a period of 5 years after the date of the most recent. See also U.S. Pat. Nos. 8,206,712 and 7,611,705, the relevant disclosures of each of which are incorporated by reference herein.

The amino acid sequences and encoding nucleotide sequences of the heavy chain variable region ($V_H$) and light chain variable region ($V_L$) of mAb7E are produced below.

```
Nucleotide sequence (SEQ ID NO: 1) and amino acid
sequence (SEQ ID NO: 2) of mAb 7E heavy chain variable
region
gaa ttg aag ctt gag gag tct gga gga ggc ttg gtg cag cct gga    45
 E   L   K   L   E   E   S   G   G   G   L   V   Q   P   G     15 gga tcc atg aaa ctc tct tgt gct gcc tct gga ttc act ttt agt    90
 G   S   M   K   L   S   C   A   A   S   G   F   T   F   S     30 gac gcc tgg atg gac tgg gtc cgc cag tct cca gag aag ggg ctt   135
 D   A   W   M   D   W   V   R   Q   S   P   E   K   G   L     45 gag tgg att gct gaa att aga agc aaa gct aat aat tat gca aca   180
 E   W   I   A   E   I   R   S   K   A   N   N   Y   A   T     60 tac ttt gct gag tct gtg aaa ggg agg ttc acc atc tca aga gat   215
 Y   F   A   E   S   V   K   G   R   F   T   I   S   R   D     75 gat tcc aaa agt ggt gtc tac ctg caa atg aac aac tta aga gct   270
 D   S   K   S   G   V   Y   L   Q   M   N   N   L   R   A     90 gag gac act ggc att tat ttc tgt acc aag tta tca cta cgt tac   315
 E   D   T   G   I   Y   F   C   T   K   L   S   L   R   Y    105 tgg ttc ttc gat gtc tgg ggc gca ggg acc acg gtc acc gtc tcc   360
 W   F   F   D   V   W   G   A   G   T   T   V   T   V   S    120 tca                                                           363
 S                                                            121
```

-continued

Nucleotide sequence (SEQ ID NO: 3) and amino acid
sequence (SEQ ID NO: 4) of mAb 7E light chain
variable region

```
gat ttt gtg atg acc cag act cca ctc act ttg tcg gtt acc att    45
 D   F   V   M   T   Q   T   P   L   T   L   S   V   T   I     15 gga caa cca gcc tcc atc tct tgc aag tca agt cag agc ctc ttg    90
 G   Q   P   A   S   I   S   C   K   S   S   Q   S   L   L    30 gat agt gat gga aag aca tat ttg aat tgg ttg tta cag agg cca   135
 D   S   D   G   K   T   Y   L   N   W   L   L   Q   R   P    45 ggc cag tct cca aag cac ctc atc tat ctg gtg tct aaa ctg gac   180
 G   Q   S   P   K   H   L   I   Y   L   V   S   K   L   D    60 tct gga gtc cct gac agg ttc act ggc agt gga tca ggg acc gat   215
 S   G   V   P   D   R   F   T   G   S   G   S   G   T   D    75 ttc aca ctg aga atc agc aga gtg gag gct gag gat ttg gga gtt   270
 F   T   L   R   I   S   R   V   E   A   E   D   L   G   V    90 tat tat tgc tgg caa agt aca cat ttt ccg tgg acg ttc ggt gga   315
 Y   Y   C   W   Q   S   T   H   F   P   W   T   F   G   G   105 ggc acc aag ctg gaa atc aaa cgg                               339
 G   T   K   L   E   I   K   R                                113
```

A functional variant (equivalent) of mAb7E has essentially the same epitope-binding specificity as mAb7E and exhibits at least 20% (e.g., 30%, 40%, 50%, 60%, 70%, 80%, 90%, or greater) of the activity of neutralizing a signaling pathway mediated by IL-20 as relative to mAb7E. In some embodiments, a functional variant of mAb7E contains the same regions/residues responsible for antigen-binding as mAb7E, such as the same specificity-determining residues in the CDRs or the whole CDRs.

In addition, determination of CDR regions in an antibody is well within the skill of the art. There are at least two techniques for determining CDRs: (1) an approach based on cross-species sequence variability (i.e., Kabat et al. Sequences of Proteins of Immunological Interest, (5th ed., 1991, National Institutes of Health, Bethesda, Md.)); and (2) an approach based on crystallographic studies of antigen-antibody complexes (Chothia et al. (1989) Nature 342:877; Al-lazikani et al (1997) J. Molec. Biol. 273:927-948)). As used herein, a CDR may refer to CDRs defined by either approach or by a combination of both approaches.

In some examples, a functional variant of mAb7E comprises a $V_H$ chain that includes a $V_H$ CDR1, $V_H$ CDR2, and $V_H$ CDR3 at least 75% (e.g., 80%, 85%, 90%, 95%, or 98%) identical to the corresponding $V_H$ CDRs of mAb7E, and a $V_L$ chain that includes a $V_L$ CDR1, $V_L$ CDR2, and $V_L$ CDR3 at least 75% (e.g., 80%, 85%, 90%, 95%, or 98%) identical to the corresponding $V_H$ CDRs of mAb7E.

Alternatively, the functional variant of mAb7E comprises a $V_H$ chain at least 75% (e.g., 80%, 85%, 90%, 95%, or 98%) identical to the $V_H$ chain (mature or precursor) of mAb7E and a $V_L$ chain at least 75% (e.g., 80%, 85%, 90%, 95%, or 98%) identical to the $V_L$ chain (mature of precursor) of mAb7E.

The "percent identity" of two amino acid sequences is determined using the algorithm of Karlin and Altschul Proc. Natl. Acad. Sci. USA 87:2264-68, 1990, modified as in Karlin and Altschul Proc. Natl. Acad. Sci. USA 90:5873-77, 1993. Such an algorithm is incorporated into the NBLAST and XBLAST programs (version 2.0) of Altschul, et al. J. Mol. Biol. 215:403-10, 1990. BLAST protein searches can be performed with the XBLAST program, score=50, word-length=3 to obtain amino acid sequences homologous to the protein molecules of interest. Where gaps exist between two sequences, Gapped BLAST can be utilized as described in Altschul et al., Nucleic Acids Res. 25(17):3389-3402, 1997. When utilizing BLAST and Gapped BLAST programs, the default parameters of the respective programs (e.g., XBLAST and NBLAST) can be used.

In other examples, a functional variant of mAb7E comprises a $V_H$ chain that includes up to 5 (e.g., 1, 2, 3, 4, or 5) amino acid residue variations in the $V_H$ CDR regions ($V_H$ CDR1, CDR2, and/or CDR3) as compared to the $V_H$ CDRs of mAb7E, and/or a $V_L$ chain that includes up to 5 (e.g., 1, 2, 3, 4, or 5) amino acid residue variations in the $V_L$ CDR regions ($V_L$ CDR1, CDR2, and/or CDR3) as compared to the $V_H$ CDRs of mAb7E.

Functional variants of mAb7E are also disclosed in U.S. Pat. No. 7,611,705 and US2011/0064731, both of which are incorporated by reference herein.

In one example, a functional variant of mAb7E is a humanized antibody derived from mAb7E. Provided below are exemplary humanized mAb7E antibodies HL1 and HL2; see also U.S. Pat. No. 8,597,647, the relevant disclosures therein are incorporated by reference.

Amino acid sequence and encoding nucleotide sequence of the $V_H$ chain of humanized anti-IL-20 antibodies HL1 and HL2:

```
                                          (SEQ ID NO: 5)
                ATG TAC TTG GGA CTG AAC TAT GTT (SEQ ID NO: 6)
                 M   Y   L   G   L   N   Y   V

TTC ATC GTT TTT CTC CTG AAT GGT GTC CAG AGT GAA
 F   I   V   F   L   L   N   G   V   Q   S   E

GTG CAG CTT GTG GAG TCT GGA GGA GGC TTG GTG CAG
 V   Q   L   V   E   S   G   G   G   L   V   Q

CCT GGA GGA TCC CTG AAA CTC TCT TGT GCT GCC TCT
 P   G   G   S   L   K   L   S   C   A   A   S

GGA TTC ACT TTT AGT GAC GCC TGG ATG GAC TGG GTC
 G   F   T   F   S   D   A   W   M   D   W   V
```

-continued

```
CGC CAG GCT TCC GGG AAG GGG CTT GAG TGG ATT GCT
 R   Q   A   S   G   K   G   L   E   W   I   A

GAA ATT AGA AGC AAA GCT AAT AAT TAT GCA ACA TAC
 E   I   R   S   K   A   N   N   Y   A   T   Y

TTT GCT GAG TCT GTG AAA GGG AGG TTC ACC ATC TCA
 F   A   E   S   V   K   G   R   F   T   I   S

AGA GAT GAT TCC AAA AAC ACC GCC TAC CTG CAA ATG
 R   D   D   S   K   N   T   A   Y   L   Q   M

AAC AGC TTA AAA ACC GAG GAC ACT GCC GTT TAT TAC
 N   S   L   K   T   E   D   T   A   V   Y   Y

TGT ACC AAG TTA TCA CTG CGT TAC TGG TTC TTC GAT
 C   T   K   L   S   L   R   Y   W   F   F   D

GTC TGG GGC CAG GGG ACC CTG GTC ACC GTC TCC TCA
 V   W   G   Q   G   T   L   V   T   V   S   S
```

The underlined region refers to the signal peptide and the boldfaced/italic regions are the CDRs. SEQ ID NOs: 8 and 7 represent the mature $V_H$ amino acid sequence (lacking the signal peptide) and its encoding nucleotide sequence, respectively.

Amino acid sequence and encoding nucleotide sequence of the $V_L$ chain (VL 2) of a humanized anti-IL-20 antibody HL2:

```
                                       (SEQ ID NO: 9)
         ATG ATG AGT CCT GCC CAG TTC CTG TTT (SEQ ID NO: 10)
          M   M   S   P   A   Q   F   L   F

CTG TTG GTG CTC TGG ATT CGG GAA ACC AAC GGT GAT
 L   L   V   L   W   I   R   E   T   N   G   D

ATC GTG ATG ACC CAG ACT CCA CTC TCT TTG TCC GTT
 I   V   M   T   Q   T   P   L   S   L   S   V

ACC CCT GGA CAA CCA GCC TCC ATC TCT TGC AAG TCA
 T   P   G   Q   P   A   S   I   S   C   K   S

AGT CAG AGC CTC TTG GAT AGT GAT GGA AAG ACA TAT
 S   Q   S   L   L   D   S   D   G   K   T   Y

TTG AAT TGG TTG TTA CAG AAG CCA GGC CAG TCT CCA
 L   N   W   L   L   Q   K   P   G   Q   S   P

CAG CAC CTC ATC TAT CTG GTG TCT AAA CTG GAC TCT
 Q   H   L   I   Y   L   V   S   K   L   D   S

GGA GTC CCT GAC AGG TTC AGT GGC AGT GGA TCA GGG
 G   V   P   D   R   F   S   G   S   G   S   G

ACC GAT TTC ACA CTG AAA ATC AGC AGA GTG GAG GCT
 T   D   F   T   L   K   I   S   R   V   E   A

GAG GAT GTT GGA GTT TAT TAT TGC TGG CAA AGT ACA
 E   D   V   G   V   Y   Y   C   W   Q   S   T

CAT TTT CCC TGG ACC TTC GGT GGA GGC ACC AAG GTG
 H   F   P   W   T   F   G   G   G   T   K   V

GAA ATC AAA
 E   I   K
```

The underlined region refers to the signal peptide and the boldfaced/italic regions are the CDRs. SEQ ID NOs: 12 and 11 represent the mature $V_L$ amino acid sequence (lacking the signal peptide) and its encoding nucleotide sequence, respectively.

Humanized antibody HL1 comprises the same $V_H$ chain as HL2 and a $V_L$ chain (SEQ ID NO:13; mature form) that is otherwise identical to the $V_L$ of HL2 except that the I residue at position 2 of mature $V_L$ of HL2 is replaced with F.

Also disclosed herein are functional variants of the above-noted humanized antibodies HL1 and HL2. Such functional variants can comprise a $V_H$ chain that comprises an amino acid sequence at least 85% (e.g., 90%, 92%, 94%, 95%, 96%, 97%, 98%, or 99%) identical to that of the $V_H$ of HL1 and HL2 (precursor or mature form; SEQ ID NO:6 and SEQ ID NO:8, respectively) and a $V_L$ chain that has an amino acid sequence at least 85% (e.g., 90%, 92%, 94%, 95%, 96%, 97%, 98%, or 99%) identical to that of the $V_L$ of HL2 (precursor or mature form; SEQ ID NO:10 and SEQ ID NO:12, respectively). These variants are capable of binding to an IL-20 molecule, particularly a human IL-20 molecule. In some examples, the variants possess similar antigen-binding affinity relative to the exemplary humanized antibody described above (e.g., having a $K_d < 4^{10}$)

(c) Antibody Preparation

Antibodies capable of interfering with the IL-20 signaling pathway as described herein can be made by any method known in the art. See, for example, Harlow and Lane, (1988) Antibodies: A Laboratory Manual, Cold Spring Harbor Laboratory, New York.

In some embodiments, antibodies specific to a target antigen (e.g., human IL-20 or IL-20R1) can be made by the conventional hybridoma technology. The full-length target antigen or a fragment thereof, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-IL-20 monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that may be used as source of antibodies encompass all derivatives, progeny cells of the parent hybridomas that produce monoclonal antibodies capable of interfering with the IL-20 signaling pathway. Hybridomas that produce such antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, SOCl, or R1N=C=NR, where R and R1 are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody. For example, the constant region may be engineered to more resemble human constant regions to avoid immune response if the antibody is used in clinical trials and treatments in humans. It may be desirable to genetically manipulate the antibody sequence to obtain greater affinity to the target antigen and greater efficacy in inhibiting the signaling pathway mediated by IL-20. It will be apparent to one of skill in the art that one or more polynucleotide changes can be made to the antibody and still maintain its binding specificity to the target antigen.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In another alternative, antibodies may be made recombinantly by phage display technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology. In one example, DNA encoding a monoclonal antibodies specific to a target antigen can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into one or more expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. See, e.g., PCT Publication No. WO 87/04462. The DNA can then be modified, for example, by substituting the coding sequence for human heavy and light chain constant domains in place of the homologous murine sequences, Morrison et al., (1984) Proc. Nat. Acad. Sci. 81:6851, or by covalently joining to the immunoglobulin coding sequence all or part of the coding sequence for a non-immunoglobulin polypeptide. In that manner, genetically engineered antibodies, such as "chimeric" or "hybrid" antibodies; can be prepared that have the binding specificity of a target antigen.

Techniques developed for the production of "chimeric antibodies" are well known in the art. See, e.g., Morrison et al. (1984) Proc. Natl. Acad. Sci. USA 81, 6851; Neuberger et al. (1984) Nature 312, 604; and Takeda et al. (1984) Nature 314:452.

Methods for constructing humanized antibodies are also well known in the art. See, e.g., Queen et al., *Proc. Natl. Acad. Sci. USA*, 86:10029-10033 (1989). In one example, variable regions of $V_H$ and $V_L$ of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human $V_H$ and $V_L$ chains having amino acid sequences that are homologous to those of the parent non-human antibody are identified from any antibody gene database using the parent $V_H$ and $V_L$ sequences as search queries. Human $V_H$ and $V_L$ acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

A single-chain antibody can be prepared via recombinant technology by linking a nucleotide sequence coding for a heavy chain variable region and a nucleotide sequence coding for a light chain variable region. Preferably, a flexible linker is incorporated between the two variable regions.

Antibodies obtained following a method known in the art and described herein can be characterized using methods well known in the art. For example, one method is to identify the epitope to which the antigen binds, or "epitope mapping." There are many methods known in the art for mapping and characterizing the location of epitopes on proteins, including solving the crystal structure of an antibody-antigen complex, competition assays, gene fragment expression assays, and synthetic peptide-based assays, as described, for example, in Chapter 11 of Harlow and Lane, Using Antibodies, a Laboratory Manual, Cold Spring Harbor Laboratory Press, Cold Spring Harbor, N.Y., 1999. In an additional example, epitope mapping can be used to determine the sequence to which an antibody binds. The epitope can be a linear epitope, i.e., contained in a single stretch of amino acids, or a conformational epitope formed by a three-dimensional interaction of amino acids that may not necessarily be contained in a single stretch (primary structure linear sequence). Peptides of varying lengths (e.g., at least 4-6 amino acids long) can be isolated or synthesized (e.g., recombinantly) and used for binding assays with an antibody. In another example, the epitope to which the antibody binds can be determined in a systematic screening by using overlapping peptides derived from the target antigen sequence and determining binding by the antibody. According to the gene fragment expression assays, the open reading frame encoding the target antigen is fragmented either randomly or by specific genetic constructions and the reactivity of the expressed fragments of the antigen with the antibody to be tested is determined. The gene fragments may, for example, be produced by PCR and then transcribed and translated into protein in vitro, in the presence of radioactive amino acids. The binding of the antibody to the radioactively labeled antigen fragments is then determined by immunoprecipitation and gel electrophoresis. Certain epitopes can also be identified by using large libraries of random peptide sequences displayed on the surface of phage particles (phage libraries). Alternatively, a defined library of overlapping peptide fragments can be tested for binding to the test antibody in simple binding assays. In an additional example, mutagenesis of an antigen binding domain, domain swapping experiments and alanine scanning mutagenesis can be performed to identify residues required, sufficient, and/or necessary for epitope binding. For example, domain swapping experiments can be performed using a mutant of a target antigen in which various fragments of the IL-20 polypeptide have been replaced (swapped) with sequences from a closely related, but antigenically distinct protein (such as another member of the neurotrophin protein family). By assessing binding of the antibody to the mutant IL-20, the importance of the particular antigen fragment to antibody binding can be assessed.

Alternatively, competition assays can be performed using other antibodies known to bind to the same antigen to determine whether an antibody binds to the same epitope as the other antibodies. Competition assays are well known to those of skill in the art.

Other IL-20 Antagonists

IL-20 antagonists other than antibodies capable of interfering with the IL-20 signaling pathway as described above can be used in the methods described herein.

In some embodiments of the invention, the IL-20 antagonist comprises at least one antisense nucleic acid molecule capable of blocking or decreasing the expression of a functional IL-20 (e.g., a human IL-20) or a subunit of an IL-20 receptor (e.g., IL-20R1). Nucleotide sequences of the IL-20 and IL-20 receptor subunits are known and are readily available from publicly available databases. See above disclosures. It is routine to prepare antisense oligonucleotide molecules that will specifically bind a target mRNA without cross-reacting with other polynucleotides. Exemplary sites of targeting include, but are not limited to, the initiation codon, the 5' regulatory regions, the coding sequence and the 3' untranslated region. In some embodiments, the oligonucleotides are about 10 to 100 nucleotides in length, about 15 to 50 nucleotides in length, about 18 to 25 nucleotides in length, or more. The oligonucleotides can comprise backbone modifications such as, for example, phosphorothioate linkages, and 2'-0 sugar modifications well known in the art.

Alternatively, IL-20/IL-20R expression and/or release can be decreased using gene knockdown, morpholino oligonucleotides, small interfering RNA (siRNA or RNAi), microRNA or ribozymes, methods that are well-known in the art. RNA interference (RNAi) is a process in which a dsRNA directs homologous sequence-specific degradation of messenger RNA. In mammalian cells, RNAi can be triggered by 21-nucleotide duplexes of small interfering RNA (siRNA) without activating the host interferon response. The dsRNA used in the methods disclosed herein can be a siRNA (containing two separate and complementary RNA chains) or a short hairpin RNA (i.e., a RNA chain forming a tight hairpin structure), both of which can be designed based on the sequence of the target gene. Alternatively, it can be a microRNA.

Optionally, a nucleic acid molecule to be used in the method described herein (e.g., an antisense nucleic acid, a small interfering RNA, or a microRNA) as described above contains non-naturally-occurring nucleobases, sugars, or covalent internucleoside linkages (backbones). Such a modified oligonucleotide confers desirable properties such as enhanced cellular uptake, improved affinity to the target nucleic acid, and increased in vivo stability.

In one example, the nucleic acid has a modified backbone, including those that retain a phosphorus atom (see, e.g., U.S. Pat. Nos. 3,687,808; 4,469,863; 5,321,131; 5,399,676; and 5,625,050) and those that do not have a phosphorus atom (see, e.g., U.S. Pat. Nos. 5,034,506; 5,166,315; and 5,792, 608). Examples of phosphorus-containing modified backbones include, but are not limited to, phosphorothioates, chiral phosphorothioates, phosphorodithioates, phosphotriesters, aminoalkyl-phosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having 3'-5' linkages, or 2'-5' linkages. Such backbones also include those having inverted polarity, i.e., 3' to 3',5' to 5' or 2' to 2' linkage. Modified backbones that do not include a phosphorus atom are formed by short chain alkyl or cycloalkyl internucleoside linkages, mixed heteroatom and alkyl or cycloalkyl internucleoside linkages, or one or more short chain heteroatomic or heterocyclic internucleoside linkages. Such backbones include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In another example, the nucleic acid used in the disclosed methods includes one or more substituted sugar moieties. Such substituted sugar moieties can include one of the following groups at their 2' position: OH; F; O-alkyl, S-alkyl, N-alkyl, O-alkenyl, S-alkenyl, N-alkenyl; O-alkynyl, S-alkynyl, N-alkynyl, and O-alkyl-O-alkyl. In these groups, the alkyl, alkenyl and alkynyl can be substituted or unsubstituted $C_1$ to $C_{10}$ alkyl or $C_2$ to $C_{10}$ alkenyl and alkynyl. They may also include at their 2' position heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide. Preferred substituted sugar moieties include those having 2'-methoxyethoxy, 2'-dimethylaminooxyethoxy, and 2'-dimethylaminoethoxyethoxy. See Martin et al., Helv. Chim. Acta, 1995, 78, 486-504.

In yet another example, the nucleic acid includes one or more modified native nucleobases (i.e., adenine, guanine, thymine, cytosine and uracil). Modified nucleobases include those described in U.S. Pat. No. 3,687,808, The Concise Encyclopedia Of Polymer Science And Engineering, pages 858-859, Kroschwitz, J. I., ed. John Wiley & Sons, 1990, Englisch et al., Angewandte Chemie, International Edition, 1991, 30, 613, and Sanghvi, Y. S., Chapter 15, Antisense Research and Applications, pages 289-302, CRC Press, 1993. Certain of these nucleobases are particularly useful for increasing the binding affinity of the antisense oligonucleotide to its target nucleic acid. These include 5-substituted pyrimidines, 6-azapyrimidines and N-2, N-6 and 0-6 substituted purines (e.g., 2-aminopropyl-adenine, 5-propynyluracil and 5-propynylcytosine). See Sanghvi, et al., eds., Antisense Research and Applications, CRC Press, Boca Raton, 1993, pp. 276-278).

Any of the nucleic acids can be synthesized by methods known in the art. See, e.g., Caruthers et al., 1992, Methods in Enzymology 211, 3-19, Wincott et al., 1995, Nucleic Acids Res. 23, 2677-2684, Wincott et al., 1997, Methods Mol. Bio. 74, 59, Brennan et al., 1998, Biotechnol Bioeng., 61, 33-45, and Brennan, U.S. Pat. No. 6,001,311. It can also be transcribed from an expression vector and isolated using standard techniques.

In other embodiments, the IL-20 antagonist comprises at least one IL-20 or IL-20R inhibitory compound. As used herein, "IL-20 inhibitory compound" or "IL-20R inhibitory compound" refers to a compound other than an anti-IL-20 or anti-IL-20R antibody that directly or indirectly reduces, inhibits, neutralizes, or abolishes IL-20/IL-20R biological activity. An IL-20/IL-20R inhibitory compound should exhibit any one or more of the following characteristics: (a) binds to IL-20 or IL-20R and inhibits its biological activity and/or downstream pathways mediated by IL-20 signaling function; (b) prevents, ameliorates, or treats any aspect of eye disease; (c) blocks or decreases IL-20 receptor activation; (d) increases clearance of IL-20 or IL-20R; (e) inhibits (reduces) IL-20 or IL-20R synthesis, production or release. One skilled in the art can prepare other small molecules inhibitory compounds.

In some embodiments, an IL-20 or IL-20R inhibitory compound is an IL-20 mutant, an IL-19 mutant, or an IL-24 mutant, which can bind to an IL-20 receptor but cannot elicit signal transduction. Such a mutant may block binding of wild type IL-20 to an IL-20 receptor thus preventing IL-20 signal transduction.

In other embodiments, the IL-20 or IL-20R inhibitory compounds described herein are small molecules, which can have a molecular weight of about any of 100 to 20,000 daltons, 500 to 15,000 daltons, or 1000 to 10,000 daltons. Libraries of small molecules are commercially available. The small molecules can be administered using any means known in the art, including inhalation, intraperitoneally, intravenously, intramuscularly, subcutaneously, intrathecally, intraventricularly, orally, enterally, parenterally, intranasally, or dermally. In general, when the IL-20-antagonist according to the invention is a small molecule, it will be administered at the rate of 0.1 to 300 mg/kg of the weight of the patient divided into one to three or more doses. For an adult patient of normal weight, doses ranging from 1 mg to 5 g per dose can be administered.

The above-mentioned small molecules can be obtained from compound libraries. The libraries can be spatially addressable parallel solid phase or solution phase libraries. See, e.g., Zuckermann et al. J. Med .Chem. 37, 2678-2685, 1994; and Lam Anticancer Drug Des. 12:145, 1997. Methods for the synthesis of compound libraries are well known in the art, e.g., DeWitt et al. PNAS USA 90:6909, 1993; Erb et al. PNAS USA 91:11422, 1994; Zuckermann et al. J. Med. Chem. 37:2678, 1994; Cho et al. Science 261:1303, 1993; Carrell et al. Angew Chem. Int. Ed. Engl. 33:2059, 1994; Carell et al. Angew Chem. Int. Ed. Engl. 33:2061, 1994; and Gallop et al. J. Med. Chem. 37:1233, 1994. Libraries of compounds may be presented in solution (e.g., Houghten Biotechniques 13:412-421, 1992), or on beads (Lam Nature 354:82-84, 1991), chips (Fodor Nature 364:555-556, 1993), bacteria (U.S. Pat. No. 5,223,409), spores (U.S. Pat. No. 5,223,409), plasmids (Cull et al. PNAS USA 89:1865-1869, 1992), or phages (Scott and Smith Science 249:386-390, 1990; Devlin Science 249:404-406, 1990; Cwirla et al. PNAS USA 87:6378-6382, 1990; Felici J. Mol. Biol. 222: 301-310, 1991; and U.S. Pat. No. 5,223,409).

In other embodiments, the IL-20 antagonists can be a polypeptide comprising an extracellular portion of an IL-20 receptor (such as IL-20 R1, IL-20R2, or IL-22R1), wherein the polypeptide specifically binds to 11-20 and blocks its interaction with one or more IL-20 receptors. In some embodiments, the extracellular portion of the IL-20 receptor is fused to a Fc domain of antibody. Examples of the soluble receptors are described in PCT WO 01/46232.

Identification of IL-20 Antagonists

IL-20 antagonists can be identified or characterized using methods known in the art, whereby reduction, amelioration, or neutralization of an IL-20 biological activity is detected and/or measured. For example, an ELISA-type assay may be suitable for qualitative or quantitative measurement of IL-20 mediated kinase activation by measuring the phosphorylation of proteins activated through an IL-20 cascade. Examples include JNK, ERK, AKT, p38, STAT3 and TRAF6.

The IL-20 antagonists can also be identified by incubating a candidate agent with IL-20 or IL-20R and monitoring any one or more of the following characteristics: (a) binding to IL-20 or IL-20R and inhibiting its biological activity and/or downstream pathways mediated by IL-20 signaling function; (b) preventing, ameliorating, or treating any aspect of eye disease; (c) blocking or decreasing IL-20 receptor activation; (d) increasing clearance of IL-20 or IL-20R; (e) inhibiting (reducing) IL-20 synthesis, production or release. In some embodiments, an IL-20 antagonist is identified by incubating a candidate agent with IL-20 or IL-20R and monitoring binding and attendant reduction or neutralization of a biological activity of IL-20 or IL-20R. The binding assay may be performed with purified IL-20 or IL-20R polypeptide(s), or with cells naturally expressing, or transfected to express, IL-20 or IL-20R polypeptide(s). In one embodiment, the binding assay is a competitive binding assay, where the ability of a candidate antibody to compete with a known IL-20 antagonist for IL-20 or IL-20R binding is evaluated. The assay may be performed in various formats, including the ELISA format. In other embodiments, an IL-20 antagonist is identified by incubating a candidate agent with IL-20 or IL-20R (e.g., IL-20R1) and monitoring attendant inhibition of IL-20R1/IL-20R2 complex formation or IL-20R2/IL-22R1 complex formation. Following initial identification, the activity of a candidate IL-20 antagonist can be further confirmed and refined by bioassays, known to test the targeted biological activities. Alternatively, bioassays can be used to screen candidates directly.

The examples provided below provide a number of assays that can be used to screen candidate IL-20 antagonists. Bioassays include but are not limited to flow cytometry of determine competitive binding of IL-20 to cells in the presence of candidate IL-20 antagonists; and inhibition of IL-20-induced apoptosis in renal epithelial cells. In addition, RT-PCR or Real-time PCR which can be used to directly measure IL-20 expression or to measure expression of genes upregulated by IL-20 such as TNFα MCP-1, IL-1β, IL-6 and VEGF.

Immune Checkpoint Inhibitors

The immune checkpoint inhibitor can be used in combination with the IL-20 antagonists of the present disclosure described herein to stimulate an immune system against cancer cells and treat a cancer. The Immune checkpoint inhibitors suitable for use in the present disclosure include antagonists of an inhibitory receptor which inhibits the PD-1, PD-L1, CTLA-4, T cell immunoglobulin-3 (TIM3), B and T lymphocyte attenuator (BTLA), V-domain Ig suppressor of T cell activation (VISTA) or lymphocyte-activation gene 3 (LAG3) pathway, such as anti-PD-1 antibodies, anti-PD-L1 antibodies, anti-CTLA-4 antibodies, anti-TIM-3 antibodies, anti-BTLA antibodies, anti-VISTA antibodies and anti-LAG-3 antibodies. Examples of PD-1 or PD-L1 inhibitors include, but are not limited to, humanized antibodies blocking human PD-1 such as pembrolizumab (anti-PD-1 Ab, trade name Keytruda®), nivolumab (anti-PD-1 Ab, Opdivo) or pidilizumab (anti-PD-1 Ab, CT-011), toripalimab (anti-PD-1 Ab, trade name Tuo Yi®), sintilimab (anti-PD-1 Ab, trade name Tyvyt®), camrelizumab (anti-PD-1 Ab), Bavencio® (anti-PD-L1 Ab, avelumab), Imfinzi® (anti-PD-L1 Ab, durvalumab), and Tecentriq® (anti-PD-L1 Ab, atezolizumab), as well as fully human antibodies such as nivolumab (anti-PD-1 Ab, trade name Opdivo®) and cemiplimab-rwlc (anti-PD-1 Ab, trade name Libtayo®). Other PD-1 inhibitors may include presentations of soluble PD-1 ligand including without limitation PD-L2 Fc fusion protein also known as B7-DC-Ig or AMP-244 and other PD-1 inhibitors presently under investigation and/or development for use in therapy. In addition, immune checkpoint inhibitors may include—without limitation—humanized or fully human antibodies blocking PD-L1 such as durvalumab and MIH1 and other PD-L1 inhibitors presently under investigation.

Combinations Comprising an IL-20 Antagonist and an Immune Checkpoint Inhibitor

The pharmaceutical combination of the present disclosure may be provided in a single formulation. In other embodiments, the pharmaceutical combination of the present disclosure may be provided in separate formulations. A pharmaceutical combination may be formulated in a variety of and/or a plurality of forms adapted to one or more preferred routes of administration. Thus, a pharmaceutical combination can be administered via one or more known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical combination, or a portion thereof, can be administered to a mucosal surface, such as by administration to, for example, the nasal or respiratory mucosa (e.g., by spray or aerosol). A pharmaceutical combination, or a portion thereof, also can be administered via a sustained or delayed release.

Use of Combinations Comprising IL-20 Antagonists and Immune Checkpoint Inhibitor for Treating Cancer The treatment with the combination of the present disclosure can treat and/or prevent a cancer. Examples of the cancer include, but are not limited to, glioblastoma, liver cancer, colorectal carcinoma, glioblastoma, gastric cancer, colorectal cancer, esophageal cancer, lung cancer, pancreatic cancer, renal cell carcinoma, benign prostate hyperplasia, prostate cancer, ovarian cancer, melanoma, breast cancer, chronic lymphocytic leukemia (CLL), Merkel cell carcinoma, Non-Hodgkin lymphoma, acute myeloid leukemia (AML), gallbladder cancer, cholangiocarcinoma, urinary bladder cancer, and uterine cancer.

Use of Combinations Comprising IL-20 Antagonists and Immune Checkpoint Inhibitor for Treating Fibrosis The treatment with the combination of the present disclosure decreases the extent of tissue fibrosis. In one embodiment, the present invention provides combinations described herein for use in the prophylaxis and/or treatment of fibrotic diseases. In a more particular embodiment, the fibrotic disease is selected from idiopathic pulmonary fibrosis, Dupuytren disease, nonalcoholic steatohepatitis, portal hypertension, systemic sclerosis, renal fibrosis, heart fibrosis, and cutaneous fibrosis. In a most particular embodiment, the fibrotic disease is idiopathic pulmonary fibrosis.

While the following examples provide further detailed description of certain aspects and embodiments of the disclosure, they should be considered merely illustrative and not in any way limiting to the scope of the claims.

EXAMPLE

The $Kras^{+/G12D}$, $Trp53^{flox/flox}$, and Pdx-1-Cre (KPC) mice maintained in C57BL/6J background contained a conditional point mutation in the transformation-related protein 53 gene (TP53R172H), and a point mutation in the KRAS gene ($KRAS^{G12D}$) both of which generated non-functional proteins.

An orthotropic tumor model was used to mimic the pancreatic cancer. KPC/Luc cells ($2 \times 10^6$) were injected orthotopically (o.c.) into the pancreas of C57BL/6J WT mice. Bioluminescent and fluorescent images were taken (IVIS 50; Xenogen, Caliper Life Sciences, Hopkinton, Mass.) to detect luminescence from KPC/Luc cells. In this study of an orthotopic model, treatments were started at day 4 and ended 4 weeks after tumor inoculation.

Figure 2:
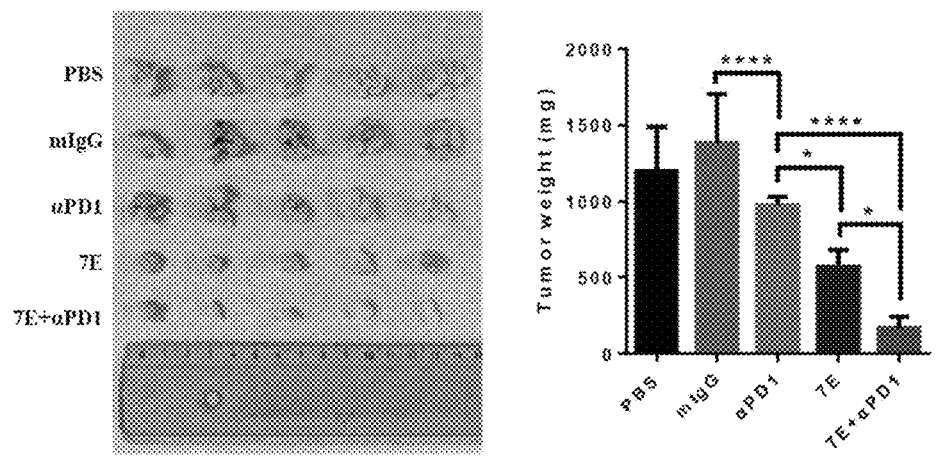
FIG. 2 shows that combined blockade of IL-20 and PD1 inhibited murine pancreatic tumor mass of PDAC orthotopic model.

To demonstrate the efficacy of the combination therapy with 7E and programmed death receptor-1 (PD1) mAb, C57BL/6J mice were randomly assigned to 5 groups (n=5pergroup), and treated with phosphate-buffered saline (PBS), 7E (6 mg/kg; intraperitoneal injection «"i.p."»), mouse immunoglobulin G (mIgG; 6 mg/kg; i.p.), PD1 mAb (200 µg/per mouse; i.p.), or 7E (mIgG; 6 mg/kg; i.p.) plus PD1 mAb (200 µg/per mouse; i.p.) twice per week for the duration. Four weeks after the inoculation, the tumor samples were taken and weighed. The efficacious results are shown in FIG. 1 and FIG. 2.

What is claimed is:

1. A method for treating a cancer or a fibrosis in a subject, wherein the method comprises administering to the subject in need thereof an effective amount of an IL-20 antagonist and an immune checkpoint inhibitor, wherein the IL-20 antagonist is an antibody that binds to IL-20 (anti-IL-20 antibody), and wherein the anti-IL-20 antibody comprises the same heavy chain complementary determining regions (CDRs) as mAb7E and the same light chain CDRs as mAb7E.

2. The method of claim 1, wherein the anti-IL-20 antibody is a full-length antibody or an antigen-binding fragment thereof.

3. The method of claim 1, wherein the anti-IL-20 antibody is, a humanized antibody, a chimeric antibody, or a single-chain antibody.

4. The method of claim 1, wherein the anti-IL-20 antibody is a humanized antibody of mAb7E.

5. The method of claim 4, wherein the humanized antibody comprises a heavy chain variable region (VH), which comprises the amino acid sequence of SEQ ID NO:8, and a light chain variable region (VL), which comprises the amino acid sequence of SEQ ID NO:12 or SEQ ID NO:13.

6. The method of claim 1, wherein the immune checkpoint inhibitor is an anti-CTLA-4 antibody, anti-PD-1 antibody or an anti-PD-L1 antibody.

7. The method of claim 1, wherein the immune checkpoint inhibitor is pembrolizumab, pidilizumab, nivolumab, durvalumab, avelumab, atezolizumab, toripalimab, sintilimab, camrelizumab or MIHI.

8. The method of claim 1, wherein the IL-20 antagonist and the immune checkpoint inhibitor are administered concurrently, separately or sequentially.

9. The method of claim 1, wherein the subject is a human patient having the cancer, which is pancreatic cancer, glioblastoma, liver cancer, colorectal carcinoma, glioblastoma, gastric cancer, colorectal cancer, esophageal cancer, lung cancer, renal cell carcinoma, benign prostate hyperplasia, prostate cancer, ovarian cancer, melanoma, breast cancer, chronic lymphocytic leukemia (CLL), Merkel cell carcinoma, Non-Hodgkin lymphoma, acute myeloid leukemia (AML), gallbladder cancer, cholangiocarcinoma, urinary bladder cancer or uterine cancer.

10. The method of claim 9, wherein the cancer is pancreatic cancer, which is adenocarcinoma or non-adenocarcinoma.

11. The method of claim 1, wherein the subject is a human patient having the fibrosis, which is a pulmonary fibrosis, idiopathic pulmonary fibrosis, Dupuytren disease, nonalcoholic steatohepatitis, liver fibrosis, portal hypertension, systemic sclerosis, renal fibrosis, cardiac fibrosis, and cutaneous fibrosis.

* * * * *